United States Patent [19]

Morita et al.

[11] Patent Number: 5,139,772
[45] Date of Patent: Aug. 18, 1992

[54] HAIR COSMETIC COMPOSITION

[75] Inventors: Kouzi Morita, Chiba; Kazuyuki Yahagi, Tokyo, both of Japan

[73] Assignee: Kao Corporation, Tokyo, Japan

[21] Appl. No.: 672,311

[22] Filed: Mar. 20, 1991

[30] Foreign Application Priority Data

Mar. 23, 1990 [JP] Japan .................................. 2-73996

[51] Int. Cl.$^5$ .......................... A61K 7/06; A61K 7/09
[52] U.S. Cl. ...................... 424/70; 424/71; 514/492
[58] Field of Search ..................... 424/70, 71

[56] References Cited

U.S. PATENT DOCUMENTS 3,152,046 10/1964 Kapral ................................. 424/70

FOREIGN PATENT DOCUMENTS 0237870 3/1987 European Pat. Off. .
0318206 5/1989 European Pat. Off. .

OTHER PUBLICATIONS

Patent Abstracts Of Japan, vol. 9, No. 228 (C-303) [1951], 13th Sep. 1985; & JP-A-60 87 208 (Shiseido K.K.) 16-5-1985 *Abstract*.

Primary Examiner—Thurman K. Page
Assistant Examiner—Sally Gardner
Attorney, Agent, or Firm—Oblon, Spivak, McClelland, Maier & Neustadt

[57] ABSTRACT

A hair cosmetic composition comprising:

(A) a dialkylene glycol monoalkyl ether of formula (I):

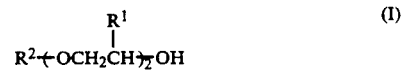

wherein $R^1$ represents a hydrogen atom or a methyl group; $R^2$ represents an alkyl group containing from 1 to 5 carbon atoms, and (B) a compound capable of liberating a di- or polyvalent metal ion in an aqueous solution is disclosed. The hair cosmetic composition imparts adequate resiliency to the hair and inhibits damage to the hair such as dryness, stiffness and incidence of split hairs.

9 Claims, No Drawings

HAIR COSMETIC COMPOSITION

FIELD OF THE INVENTION

The present invention relates to a hair cosmetic composition and more particularly to a hair cosmetic composition which imparts adequate resiliency to the hair and inhibits damage to the hair, such as dryness, bristling and incidence of split hairs.

BACKGROUND OF THE INVENTION

The hitherto-known technology for imparting resiliency to the hair includes, for example, the method in which a high molecular substance is included in hair cosmetic compositions with the result that the substance is adsorbed on the surface of the hair, thereby rendering the hair resilient. Another method involves including an astringent substance in hair cosmetic compositions which makes the hair astrictive.

However, these methods have several disadvantages. When the first-mentioned method is used to apply a hair cosmetic which is to be washed off, such as a hair rinse, it accomplishes the anticipated effect only to a limited extent because of inadequate adsorption of the high molecular weight substance on the hair and produces dryness, stiffness and other undesirable effects on the hair, thus giving the hair a poor feel. The second-mentioned method is also disadvantageous from the point of view that it causes serious damage to the hair, such as dryness and stiffness which produce a poor tactile sensation.

Therefore, development of a hair cosmetic which imparts adequate resiliency to the hair without damaging it has been keenly demanded.

SUMMARY OF THE INVENTION

Accordingly, one object of the present invention is to provide a hair cosmetic composition which imparts resiliency to the hair, prevents hair injury due to swelling of the hair on rinsing, and confers conditioning effects on the hair after drying because of its emollient action and which does not cause dryness and stiffness of the hair.

Briefly, this object and other objects of the present invention as hereinafter will become more readily apparent can be attained by a hair cosmetic composition comprising:

(A) a dialkylene glycol monoalkyl ether of formula (I):

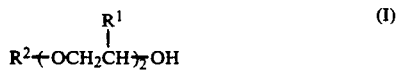

wherein $R^1$ represents a hydrogen atom or a methyl group; $R^2$ represents an alkyl group containing from 1 to 5 carbon atoms, and (B) a compound capable of liberating a di- or polyvalent metal ion in an aqueous solution.

DETAILED DESCRIPTION OF THE PREFERRED EMBODIMENTS

Referring to formula (I) above, component (A) includes, for example, diethylene glycol monomethyl ether, diethylene glycol monoethyl ether, diethylene glycol monopropyl ether, diethylene glycol monobutyl ether, diethylene glycol monopentyl ether, diethylene glycol monoisopropyl ether, diethylene glycol mono-t-butyl ether, dipropylene glycol monomethyl ether, dipropylene glycol monethyl ether, dipropylene glycol monopropyl ether, dipropylene glycol monobutyl ether, dipropylene glycol monopentyl ether, dipropylene glycol monoisopropyl ether, dipropylene glycol mono-t-butyl ether, and the like. Particularly preferred are diethylene glycol monoethyl ether, diethylene glycol monopropyl ether, and diethylene glycol monobutyl ether.

The proportion of component (A) in the hair cosmetic composition of the invention is virtually optional but, in ordinary formulations, may range from 1 to 90% by weight, preferably from 1 to 50% by weight and, more preferably from 2 to 20% by weight, based on the total weight of the composition. At levels below 1% by weight, the desired effects cannot be accomplished to a sufficient extent.

The compound capable of liberating a di- or polyvalent metal ion in an aqueous solution, i.e., component (B), may be substantially any compound that is soluble in an aqueous medium containing component (A) and which liberates a di- or polyvalent metal ion in the resulting aqueous solution. As such, component (B) can be selected from among the oxides, halides, hydroxides, inorganic acid salts, organic acid salts, and the like, of an alkaline earth metal such as calcium, magnesium, and the like; a Zn group element such as zinc and the like; an Al group element such as aluminum and the like; a Sn group element such as lead and the like; an Fe group element such as iron and the like; a Cu group element such as copper; manganese, and so on. The inorganic acids which form such metal salts include nitrous acid, sulfuric acid, phosphoric acid, boric acid, carbonic acid and so on. The organic acids which form such metal salts include acetic acid, oxalic acid, hydroxycarboxylic acids, pyrrolidonecarboxylic acids and so on.

Component (B) is added to a hair cosmetic composition in a proportion of, as the metal, from 0.005 to 20% by weight, preferably from 0.005 to 5.0% by weight and more preferably from 0.05 to 1.0% by weight, based on the total weight of the composition. However, where the final cosmetic product is to be diluted before application to the hair, the proportions of components (A) and (B) are not limited to the above ranges, but may be larger.

The term "cosmetic composition" as used herein means any and all types of cosmetic products that are applied to the hair and include, for example, preshampoos, shampoos, hair rinses, hair conditioners, hair treatments, set lotions, blow styling lotions, hair sprays, styling foams, styling jellies, hair liquids, hair tonics and hair creams. There is no limitation on formulation, either. Thus, according to intended uses, the hair cosmetic composition of the invention can be provided in a variety of formulations such as aqueous solutions, ethanolic solutions, emulsions, suspensions, gels, liquid crystals, solids, aerosols and so on.

The hair cosmetic composition of the present invention may contain, in addition to the essential components (A) and (B), those ingredients which are commonly used in hair cosmetics.

By way of illustration, the hair cosmetic composition of the invention may contain various anionic surfactants such as alkylbenzenesulfonates, alkylethersulfates, olefin sulfonates, α-sulfo-fatty acid esters, amino acid surfactants, phosphate ester surfactants, sulfosuccinate ester surfactants, etc.; cationic surfactants such as straight-chain and/or branched alkyl quaternary ammonium salts etc. (as described, for example, in JP-A-61-267505 (corresponding to U.S. Pat. No. 4,711,776), JP-A-1-106811 (corresponding to U.S. Pat. No. 4,910,013) and JP-A-1-117821) (the term "JP-A" as used herein means "unexamined published Japanese Patent Application"); amphoteric surfactants such as sulfonic acid surfactants, betaine surfactants, alkylamine oxides, imidazoline surfactants etc.; and nonionic surfactants such as polyoxyethylene alkyl ethers, polyoxyethylene alkylphenyl ethers, alkanolamides and the corresponding alkylene oxide adducts, fatty acid esters of polyhydric alcohols, sorbitan fatty acid esters, alkylsaccharide surfactants and so on. These additives can be used independently or in combination according to the desired properties of the hair cosmetic products. Particularly when the hair cosmetic composition of the present invention is provided in the form of a shampoo, the consideration of irritancy to the skin and hair favors the use of amino acid surfactants, phosphate ester surfactants, α-sulfofatty acid esters, imidazoline surfactants and alkylsaccharide surfactants. The hair cosmetic composition of the invention may generally contain such surfactants in a proportion of from 0.01 to 40.0% by weight based on the total weight of the composition. The preferred level of addition is from 5 to 30% by weight for detergent products and from 0.05 to 20.0% by weight for other hair cosmetics.

For the purpose of improving the handle or feel of the hair and skin, the hair cosmetic can contain one or more cationic polymers such as cationized cellulose derivatives, cationic starch, cationized guar gum derivatives, diallyl quaternary ammonium salt-acrylamide copolymer, quaternized polyvinylpyrrolidone derivatives, polyglycol polyamine condensates and so on. The preferred examples of such cationic polymers include cationized celluloses with molecular weights of from about 100,000 to about 3,000,000, cationized starches with degrees of cationization of from about 0.01 to about 1, cationized quar gums with degrees of cationization of from about 0.01 to about 1 (for example, Jaguar, a product of Celanese, and the like), diallyl quaternary ammonium salt-acrylamide copolymers with molecular weights of from about 30,000 to about 2,000,000, quaternized polyvinylpyrrolidone derivatives with molecular weights of from about 10,000 and about 2,000,000 and cationic nitrogen contents of the vinyl polymer moiety of from 0.04 and 0.2%, alkyl ($C_{6-20}$) polyglycol polyamine condensates, adipic acid-dimethylaminohydroxypropyldiethylenetriamine copolymer (Cartaretin, a product of Sandoz, and the like) and the cationic polymers as described, for example, in JP-A-531-139734 (corresponding to U.S. Pat. Nos. 4,240,450 and 4,719,099) and JP-A-60-36407 (corresponding to U.S. Pat. 4,597,962). The proportion of such cationic polymers in the hair cosmetic composition of the present invention is preferably from 0.05 to 20.0% by weight and more preferably from 0.2 to 10.0% by weight, based on the total weight of the composition.

The hair cosmetic composition of the present invention may further contain, for improved feel to the hair and skin, one or more silicone derivatives such as dimethyl polysiloxane, methyl phenyl polysiloxane, amino-modified silicones, fatty acid silicones, alcohol-modified silicones, aliphatic alcohol-modified silicones, polyether-modified silicones, epoxy-modified silicones, fluorine-modified silicones, cyclic silicones, alkyl-modified silicones and so on. These silicone derivatives may be single substances or latex compositions prepared by emulsion polymerization according to the method as described, for example, in the specification of JP-B-56-38609 (the term "JP-B" as used herein means "examined Japanese Patent Publication"). Among said silicone derivatives, dimethyl polysiloxanes (degrees of polymerization are not less than 500), polyether-modified silicones, amino-modified silicones and cyclic silicones are preferred for imparting a good feel to the hair. The proportion of such silicone derivatives in the hair cosmetic composition of the present invention is preferably from 0.01 to 20.0% by weight and more preferably from 0.05 to 10.0% by weight, based on the total weight of the composition.

The hair cosmetic composition of the present invention may further contain those ingredients which are commonly incorporated in hair cosmetics, including feel-improving agents such as higher fatty acid salts, alkylamine oxides, fatty acid alkanolamides, squalene, lanoline, etc.; humectants such as propylene glycol, glycerol, sorbitol, and amide derivatives of formula (II):

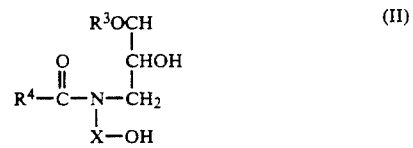

wherein $R^3$ represents a saturated or unsaturated, straight-chain or branched hydrocarbon group which contains from 10 to 26 carbon atoms; $R^4$ represents a saturated or unsaturated, straight-chain or branched hydrocarbon group which contains from 9 to 25 carbon atoms; X represents $CH_2)_m$, represents an integer of from 2 to 6; rheology (viscosity) modifiers such as methylcellulose, carboxyvinyl polymers, hydroxyethylcellulose, polyoxyethylene glycol distearate, ethanol, and the like; pealing agents; perfumes; dyes; ultraviolet absorbers; antioxidants; germicides such as triclosan, triclocarban, and the like; antiinflammatory agents such as potassium glycyrrhizinate, tocopherol acetate, and the like; antidandruff agents such as pyrithione zinc, octopirox, and the like; and preservatives such as methylparaben, butylparaben and so on. These additives can be used in appropriate amounts which do not interfere with the effects of the invention.

While the hair cosmetic composition of the present invention can be manufactured by the established procedures, it is preferably adjusted to pH 3–10, particularly pH 4–8, with an acid or alkaline substance which is generally used in hair cosmetics.

Having generally described this invention, a further understanding can be obtained by reference to certain specific examples which are provided herein for purposes of illustration only and are not intended to be limiting unless otherwise specified.

EXAMPLE 1

The hair cosmetic compositions of Table 1 were prepared and evaluated. The results are shown in Table 1.

EVALUATION METHOD

About 20 g of hair (about 15–20 cm in length) from a Japanese female who had not undergone cosmetic treatment such as cold waving, bleaching, etc., were bundled, shampooed and evenly coated with 2 g of the test hair cosmetic composition. The coated hair was rinsed in running water for 30 seconds, towel-dried and further dried with a hair dryer. The hair was then evaluated for softness, greasy felling, smoothness, resiliency and incidence of split hairs according to the following criteria.

(1) Softness:
A: Very soft
B: Soft
C: Intermediate between hard and soft
D: Hard (2) Greasy feeling:
A: Minimal
B: A little
C: Equivocal
D: Greasy (3) Smoothness:
A: Very smooth
B: Smooth
C: Equivocal
D Not smooth (4) Resiliency:
A: Very resilient
B: Resilient
C: Equivocal
D: Not resilient (5) Incidence of split hairs:
Using the hair bundle treated in the same manner as above, the incidence of split hairs after brushing for predetermined times was compared with the prebrushing baseline and rated according to the following criteria.
A: No increase in split hairs
B: Little increase in split hairs
C: A slight increase in split hairs
D: A marked increase in split hairs

TABLE 1

| Component | Product of the Invention 1 (% by weight) | Product of the Invention 2 (% by weight) | Comparative Product 1 (% by weight) | Comparative Product 2 (% by weight) |
|---|---|---|---|---|
| Stearyltrimethyl-ammonium chloride | 1 | 1 | 1 | 1 |
| Stearyl alcohol | 3 | 3 | 3 | 3 |
| Dipropylene glycol monoethyl ether | 5 | 20 | — | — |
| Aluminum Sulfate | 0.1 | — | 0.1 | — |
| Magnesium chloride | — | 1.0 | — | 1.0 |
| Purified water | Balance | Balance | Balance | Balance |
| Softness | B | A | C | C |
| Greasy feeling | B | A | D | D |
| Smoothness | B | A | B | D |
| Resiliency | B | A | B | B |
| Incidence of Split hairs | B | A | D | D |

EXAMPLE 2

| | Product of the Invention 3 (% by weight) | Comparative Product 3 (% by weight) |
|---|---|---|
| Cetostearyl alcohol | 5 | 5 |
| Polyoxyethylene (12) oleyl ether | 2 | 2 |
| Diethylene glycol monoethyl ether | 20 | 20 |
| Aluminum di-dl-pyrrolidone-carboxylate | 0.1 | — |
| Purified water | Balance | Balance |

-continued

| | Product of the Invention 3 (% by weight) | Comparative Product 3 (% by weight) |
|---|---|---|
| Total | 100 | 100 |

A panel of 10 users was requested to use each of the test hair cosmetic compositions after shampooing, rinsing off and drying the hair with an electric hair dryer. Then, a paired test was performed. As a result, 8 of the 10 panelists favored Product of the Invention 3 in terms of resiliency-imparting effect, with a significant difference.

EXAMPLE 3

| Hair treatment: | Product of the Invention 4 (% by weight) | Comparative Product 4 (% by weight) |
|---|---|---|
| N-(2-Dodecyl)hexadecyl-N,N,N-trimethylammonium chloride | 2 | 2 |
| Cetostearyl alcohol | 5 | 5 |
| Diethylene glycol monethyl ether | 20 | — |
| Aluminum di-dl-pyrrolidone carboxylate | 0.5 | — |
| Purified water | Balance | Balance |
| Total | 100 | 100 |

A panel of 10 users was asked to shampoo the hair, apply each hair treatment, rinse, and dry with an electric hair drier. A paired sensory test was performed for softness, greasy feeling, moist feeling, smoothness and resiliency. As a result, 9 of the 10 panelists favored Product of the Invention 4 to Comparative Product 4 in terms of the average score for all the evaluation items.

EXAMPLE 4

| Styling lotion: | (% by weight) |
|---|---|
| (1) Dipropylene glycol monethyl ether | 20.0 |
| (2) Acrylic resin fluid | 5.0 |
| (3) Polyethylene glycol | 1.0 |
| (4) Methacrylate polymer | 1.0 |
| (5) Iron chloride (III) | 1.0 |
| (6) Ethanol | 20.0 |
| (7) Perfume | 0.3 |
| (8) Water | Balance |
| Total | 100 |

EXAMPLE 5

| Conditioning mousse: | | (% by weight) |
|---|---|---|
| (1) | N-(2-Decyl)tetradecyl-N,N,N-trimethylammonium chloride | 0.5 |
| (2) | Octyl dodecyl myristate | 1.0 |
| (3) | Dipropylene glycol | 1.0 |
| (4) | Diethylene glycol monopentyl ether | 20.0 |
| (5) | Calcium carbonate | 5.0 |
| (6) | Glycerol | 2.5 |
| (7) | Liquid paraffin | 2.5 |
| (8) | Polyoxyethylene-sorbitan monostearate | 0.2 |
| (9) | Ethanol | 5 |
| (10) | Methylparaben | 0.1 |
| (11) | Perfume | 0.1 |
| (12) | Propellant (LPG) | 10 |
| (13) | Water | Balance |

-continued

| Conditioning mousse: | (% by weight) |
|---|---|
| Total | 100 |

EXAMPLE 6

| Shampoo: | | (% by weight) |
|---|---|---|
| (1) | N-Lauroyl-N'-carboxymethyl-N'-(2-hydroxyethyl)ethylenediamine TEA salt | 10 |
| (2) | Diethylene glycol monobutyl ether | 5 |
| (3) | Disodium polyoxyethylene(5)-laurylsulfosuccinate | 5 |
| (4) | Laurylic acid diethanolamide | 2 |
| (5) | Coconut oil fatty acid amide propylbetaine | 2 |
| (6) | Distearyldimethylammonium chloride | 0.1 |
| (7) | Cationized cellulose (Polymer JR400, a product of UCC) | 0.15 |
| (8) | Aluminum di-dl-pyrrolidone-carboxylate | 0.5 |
| (9) | Perfume | 0.5 |
| (10) | Dye | q.s. |
| (11) | Water | Balance |
| | Total | 100 |

While the invention has been described in detail and with reference to specific embodiments thereof, it will be apparent to one skilled in the art that various changes and modifications can be made therein without departing from the spirit and scope thereof.

What is claimed is:

1. A hair cosmetic composition comprising:
(A) a dialkylene glycol monoalkyl ether of formula (I):

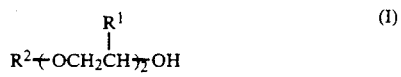

$$R^2\text{-}(OCH_2CH_2)_2\text{-}OH \quad (I)$$

wherein $R^1$ represents a hydrogen atom or a methyl group; $R^2$ represents an alkyl group containing from 1 to 5 carbon atoms, and (B) a compound selected from the group consisting of oxides, halides, hydroxides, inorganic acid salts and organic acid salts of alkaline earth metals, zinc group metals, aluminum group metals, tin group metals, iron group metals, Cu group metals and manganese.

2. The composition of claim 1, which further comprises at least one ingredient selected from the group consisting of feel-improving agents, humectants, rheology modifiers, pealing agents, perfumes, dyes, ultraviolet absorbers, antioxidants, permicides, antiinflammatory agents, antidandruff agents and preservatives.

3. The composition of claim 1, wherein said component (B) is present in an amount of from 0.005 to 20% by based on the total weight of the composition.

4. The composition of claim 3, wherein said amount of component (B) is 0.005 to 5.0% by weight based on the total weight of the composition.

5. The composition of claim 1, wherein said dialkylene glycol monoalkyl ether is diethylene glycol monomethyl ether, diethylene glycol monoethyl ether, diethylene glycol monopropyl ether, diethylene glycol monobutyl ether, diethylene glycol monopentyl ether, diethylene glycol monoisopropyl ether, diethylene glycol mono-t-butyl ether, dipropylene glycol monomethyl ether, dipropylene glycol monoethyl ether, dipropylene glycol monopropyl ether, dipropylene glycol monobutyl ether, dipropylene glycol monopentyl ether, dipropylene glycol monoisopropyl ether, or dipropylene glycol mono-t-butyl ether.

6. The composition of claim 1, wherein the amount of component (A) ranges from 1 to 90% by weight based on the total weight of the composition.

7. The composition of claim 6, wherein said amount of component (A) ranges from 1 to 50% by weight based on the total weight of the composition.

8. The composition of claim 1, which further comprises at least one anionic, cationic, amphoteric or nonionic surfactant.

9. The composition of claim 8, wherein the amount of said surfactant ranges from 0.01 to 40.0% by weight based on the total of the composition.

* * * * *